United States Patent [19]

McFadden

[11] Patent Number: 4,935,026
[45] Date of Patent: Jun. 19, 1990

[54] ARTICULATABLE, ROTATABLE, SURGICAL CLAMPING DEVICE

[76] Inventor: Joseph T. McFadden, 513 Mowbray Arch, Norfolk, Va. 23507

[21] Appl. No.: 268,382

[22] Filed: Nov. 7, 1988

Related U.S. Application Data

[63] Continuation-in-part of Ser. No. 130,471, Dec. 9, 1987, Pat. No. 4,856,518.

[51] Int. Cl.$^5$ ............................................. A61B 17/00
[52] U.S. Cl. ..................................................... 606/142
[58] Field of Search .................................. 128/321–324, 128/346, 303 R; 292/256–257; 433/153, 159, 160, 162; 606/139, 142

[56] References Cited

U.S. PATENT DOCUMENTS

| | | | |
|---|---|---|---|
| 426,074 | 4/1890 | Scheffer | 433/160 |
| 1,197,648 | 9/1916 | Meyers | 433/153 |
| 2,467,969 | 4/1949 | Debrot | 433/160 |
| 2,507,710 | 5/1950 | Grosso | 128/321 |
| 3,506,012 | 4/1970 | Brown | 128/346 |
| 3,805,792 | 4/1974 | Cogley | 128/346 |
| 4,602,631 | 7/1986 | Fanatsu | 128/321 |
| 4,733,664 | 3/1988 | Kirsch et al. | 128/321 |

Primary Examiner—Max Hindenburg
Attorney, Agent, or Firm—Cushman, Darby & Cushman

[57] ABSTRACT

An articulatable, rotatable, surgical clamping device which includes an upper handle portion connected to a fixed collar which acts on a center spindle element. The center spindle element subtended by a fixed collar slidingly engages clamp extender elements so as to alternately pull them towards each other or apart so as to clamp the clamping elements. The clamp extender elements being separated from the handle elements by a rotatable cuff which allows free rotation between the plane of articulation of the clamp elements and the plane containing the handle portions.

2 Claims, 2 Drawing Sheets

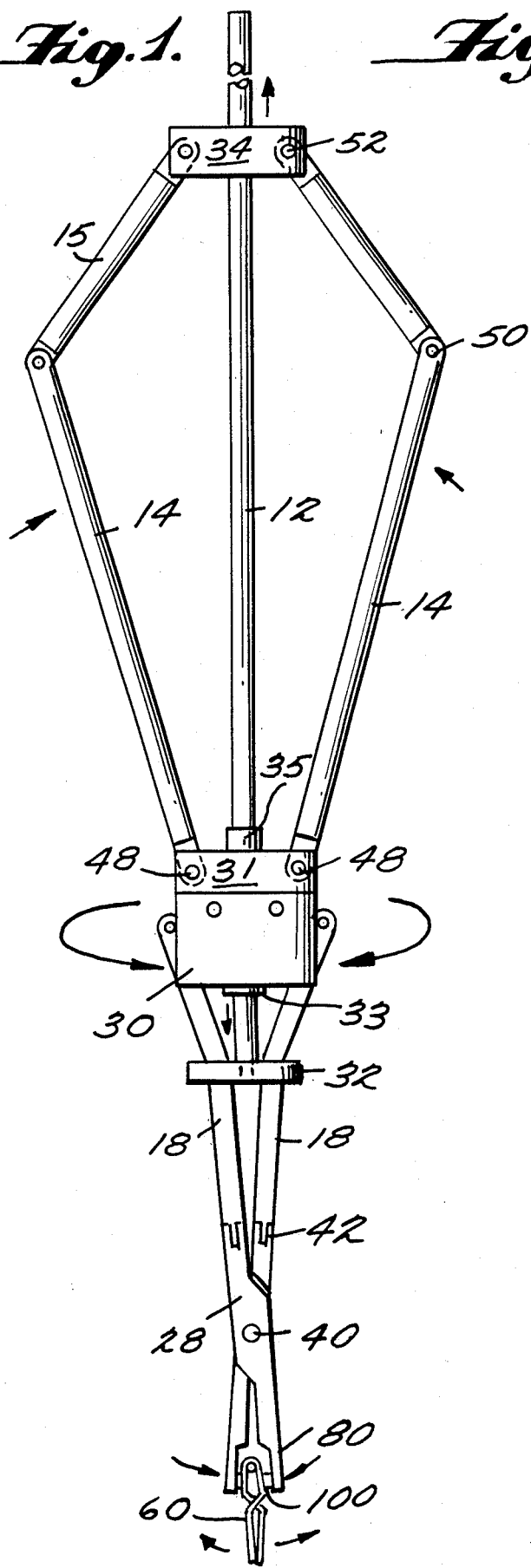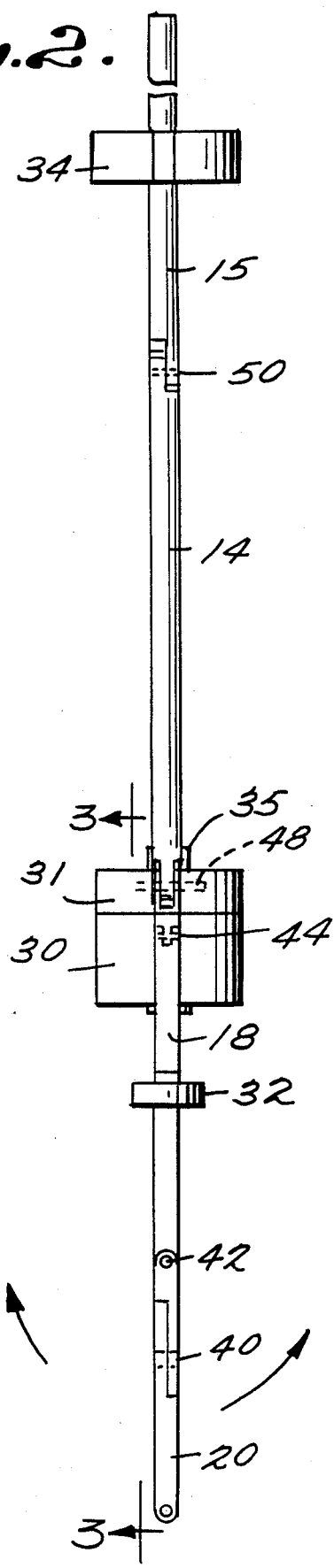

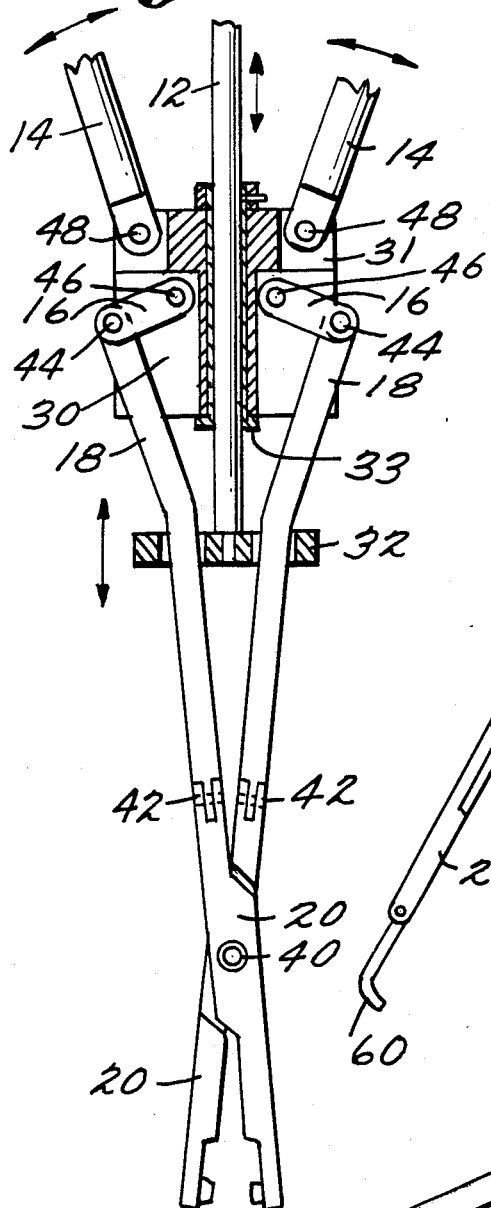
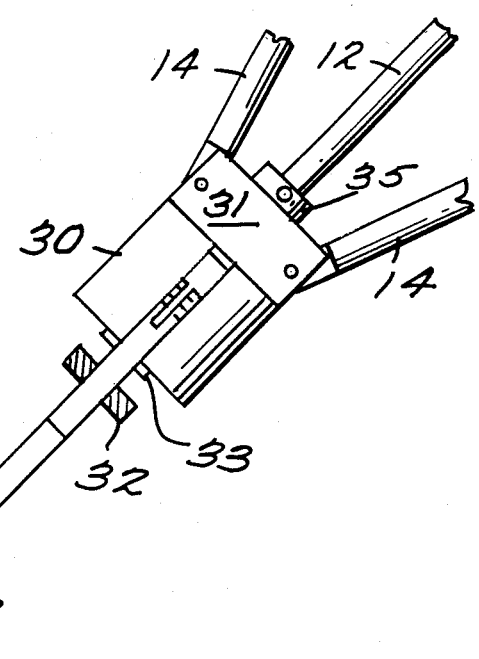
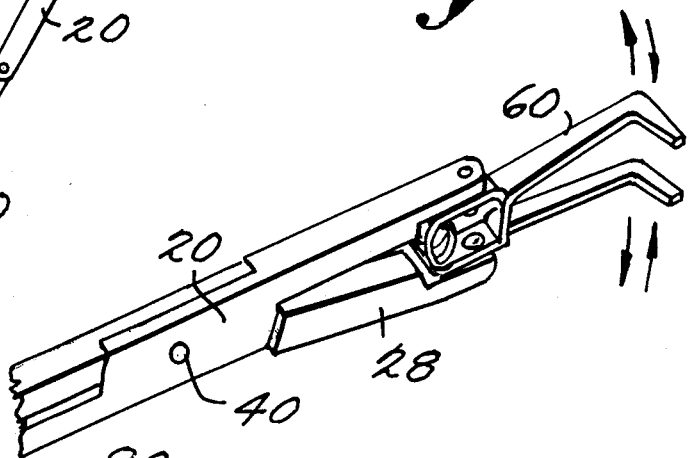
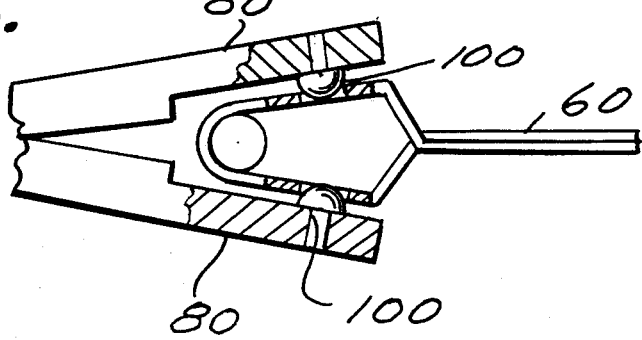

ARTICULATABLE, ROTATABLE, SURGICAL CLAMPING DEVICE

This is a continuation-in-part of U.S. application Ser. No. 07/130,471, filed Dec. 9, 1987, now U.S. Pat. No. 4,856,518.

FIELD OF THE INVENTION

The present invention relates to a clamping device for use in the placing of a surgical clip during a surgical procedure. More particularly, the present invention relates to a device which is conveniently rotatable at a lower portion thereof and articulatable so that an attachable surgical clamping device may be accurately placed from virtually any approach to the point of application.

BACKGROUND OF THE INVENTION

Prior art surgical clamps for use in applying surgical clips have, for the most part, comprised extended scissor-type lockable clamps with neither lower portion rotation or articulation. Owing to their simplified construction, the prior art clamping devices have been fairly inconvenient to use. Their rigidity, or single dimension flexibility, permit only a limited flexibility for the user and no means of pivoting the clamping device on the surgical clip or easily releasing the clip from the clamping device. The user, surgeon, must either make room for the use of the clamping device or place the placeable clamp from a non-advantageous angle.

With the increasing complexity of many surgical procedures, i.e., in that they are performed while looking through a microscope, it is most difficult to properly execute a close-quartered maneuver with inflexible instruments. Hence, the need for a clamping device with enhanced adaptability and flexibility is becoming greater as medical science enlarges the frontiers of surgical techniques.

SUMMARY OF THE INVENTION

The present invention seeks to avoid the inflexibility of prior art surgical clamping devices. To this end, a clamping device according to the present invention combines both articulation and rotation of the lower clamping elements with regard to the manipulated handle elements, as well as easy engagement, manipulation and release of the clamping device at the area where the surgical clip and the clamping device come in contact. In this manner, a user of a clamping device according to the present invention is able to precisely and advantageously place an attachable surgical clipping device (or, for that matter, any surgical device) in the surgical area with a minimum of inconvenience.

Other objects, features and characteristics of the present invention, as well as the methods in operation and functions of the related elements of the structure, and to the combination of parts and economies of manufacture, will become apparent upon consideration of the following description and the appended claims with reference to the accompanying drawings, all of which form a part of the specification, wherein like reference numerals designate corresponding parts in the various figures.

BRIEF DESCRIPTION OF THE DRAWINGS

FIG. 1 is an elevational view of a surgical clamping device according to the present invention.

FIG. 2 is a side view of a surgical clamping device according to the present invention.

FIG. 3 is a sectional view of the clamping device along line 3—3 of FIG. 2.

FIG. 4 is a perspective view of a surgical clamping device according to the present invention shown with the lower joint articulated and rotatively displaced from the plane of the handle elements.

FIG. 5 is a perspective view of the clamping elements of the present invention engaged with a placeable surgical clip.

FIG. 6 is a side view of the clamping elements engaged with a placeable surgical clip, showing the two opposing semi-spherical protrusions on the inner sides of the clamping elements positioned at the two circular holes on each side of the surgical clip.

DETAILED DESCRIPTION OF THE PREFERRED EMBODIMENT

With reference to drawing FIG. 1, the clamping device 10 will be described. Although the clamping device 10 comprises many elements, they can be broken down in series according to their function. In this manner, reference numerals 12–20 designate linearly longitudinal elements, connected by joints 40–52, which perform the manipulating and clamping functions of the present invention. To further assist the clamping action, and also to provide rotation, the sliding collars and rotating cuffs are designated generally by reference numerals 30–34. In combination, these elements cooperate to provide a surgical clamping device which conveniently is articulable and rotatable and can be manipulated by a single hand.

The center longitudinal spindle 12 is subtended at one end by lower sliding collar 32 and at its top end by fixed collar 34. Spindle element 12 is of any convenient length depending on the size and range of clamping action desired for a particular clamping device. Also, any combination of handle element lengths 14 and 15, which are connected to collar 34, with a chosen length of spindle 12 which results in a conveniently usable size configuration for a given operator's hand is recommended. Handle elements 14 and 15 extend from fixed collar 34 in an articulated manner such that relative motion between handle elements 14 and 15 creates longitudinal movement in upper rotatable cuff portions 31 along the length of spindle 12. Both of the rotatable cuff portions 31 and 30 are slidingly engaged around spindle element 12 and are loosely fixed together longitudinally by sleeve 33 and locking collar 35. In this manner, manipulation of handle elements 14 and 15, either towards one another or apart, results in the slight movement of upper rotator cuff 31 along spindle 12 towards or away from lower cuff portion 30. Lower rotatable cuff portion 30 has pivotally connected thereto, through extension elements 16 (shown in FIG. 3), clamp extending elements 18. The clamp extender elements are connected in an articulated manner to lower cuff portion 30 (discussed infra in relation to FIG. 3) so as to allow sliding movement of lower sliding collar 34 to alternatively spread or draw together clamp extenders 18.

It should be noted, that upper and lower rotatable cuff portions 30 and 31 are capable of slight separation along sleeve 33 and are therefore independently rotatable thereabout. As will be explained elsewhere in this specification, this feature allows for free rotation of the cuff portions when handle portions 14 and 15 are released and requires only slight pressure on handles 14 and 15, forcing cuffs 30 and 31 together, to maintain a rotated position of the lower clamp portion with respect to the handle elements when desired.

Clamp extender elements 18 are connected to clamping elements 20 at joint 42. The clamping elements 20 are related by a conventional scissors type joint with their jaw ends fitted with jaw elements suitable for the desired task. For a given procedure, the jaw elements may be serrated, clamp-engaging, cutting, etc. depending on the desired use. In the instant embodiment, each jaw element 80 is constructed with a semi-spherical protrusion 100 extending inward from its inner surface which interacts with placeable surgical clip 60 illustrated at the bottom of FIG. 1.

FIG. 2 is a side view of a surgical clamping device according to the present invention, and illustrates the relative direction of articulation permitted at joint 42. This relative plane of articulation can, of course, be altered to any desired plane relative to the plane of the clamping elements 14 and 15 by rotation between cuff elements 30 and 31.

All of the joints, reference numerals 40–52, are illustrated as simple pin and slot connectors in this embodiment. Of course, given the precise nature of such an instrument, it may be desirous for a more refined joint type to be used. Additionally, the joint type may be such that a limited range of movement is provided with specific gradations separating degrees of movement therein. Coversely, if it is desirous to use the clamping device for other precision work, i.e., in the repair of electronics components with limited space availability, the relative proportions, joint types, and degrees of movement would necessarily be adjusted to suit.

FIG. 3 is a sectional view along line 3—3 of FIG. 2. The upper and lower rotatable cuff portions 31 and 30 are both sectioned as well as lower sliding collar 32 and locking collar 35 and sleeve 33. In this view, the details of the connections of clamp extenders 18 to the lower rotatable cuff portion 30 are easily seen. An additional pin joint, 46, is located within lower cuff portion 30 and allows the controlled spreading or contracting of clamp extender elements 18 via connection to lower extension members 16. These members are related in this same manner as handle elements 14 and 15, the only difference being that the collar (the lower rotatable cuff portion 30) to which they are attached is movable along spindle 12.

In operation, sliding collar 32 moves along clamp extenders 18 and alternatively spreads or pulls them closer together. This movement is translated through joints 42 to clamping elements 20.

Spindle 12 is moved upwardly by clamping action on handle elements 14 and 15, and the handle elements, through joints 48, at the same instant, push downwardly on upper rotatable cuff portion 31. This pressure on rotatable cuff portion 31 urges cuff 31 against cuff portion 30 to stop relative rotation therebetween. As spindle 12 moves upwardly, it also pulls collar 32 upwardly along clamp extenders 18 drawing them towards one another thus urging clamp elements 20 together in a clamping action. During this clamping motion, the rotation between upper and lower cuff portions 30 and 31 around sleeve 33 ceases and a desired plane of articulation of clamping elements 20 with regard to the clamp extenders 18 is maintained. Joint 42 may be constructed as an interference-type hinge such that a certain amount of force is required before articulation is achieved. In this manner, a rotatable, articulable clamping device is achieved which allows convenient operator placement of surgical or other devices which require precision placement.

FIG. 4 illustrates upper and lower cuff portions 31 and 30 in a rotatively displaced position with the lower cuff 30 rotated 90 from upper cuff 31, thus enabling an operator's hand to be vertically oriented while the clamp portions are horizontally oriented. Also illustrated is the relative articulation between clamp extenders 18 and clamp elements 20. Thus, an operator may conveniently position clip 60 within the clamping elements 20, manipulate articulated joint 42 and rotation cuff 30 to obtain a desired configuration for the clamping device 10, and then single-handedly manipulate and release the clipping device 60 in a desired location.

FIG. 5 is an enlarged view of clamping elements 20 engaged with placeable surgical clip 60. The surgical clip 60 is a spring device which resiliently urges its L-shaped clipping portions against one another in order to secure itself at a desired location. Clamping elements 20 must engage the sides of clip 60 and urge same towards each other so that the clip may be opened. In this manner, clip 60 provides its own spring release action for the clamp placing device 10.

Clamp 10 may also be provided with its own spring release means to obtain resilient response action as opposed to manual actuation. A helically wound spring may be placed around spindle 12 between cuff 30 and collar 32 so as to provide a resilient force against an operator's grip. Another leaf-type spring may also be positioned around spindle 12 directly beneath fixed collar 34 to urge handle elements 15 into a spread position.

The sequence of operation of the articulable, rotatable, surgical clamping device will now be described with reference to FIG. 1. Handle elements 14 and 15 are spread from one another simultaneously urging fixed collar 34 downward. Since collar 34 is fixed to spindle 12, spindle 12 is also urged in a downward direction. Attached to the bottom end of spindle 12 is sliding collar 32 which is also urged downwardly between clamp extenders 18. The downward movement of collar 32 spreads clamp extenders 18 which in turn acts to spread clamp extenders 20. A placeable surgical clip 60 is then inserted in between the jaw elements of clamping element 20. The resiliency of clip 60 may in and of itself keep the clip maintained in position between clamping elements 20, or resilient spring members may be provided to urge clamping elements 20 together so as to hold clip 60 in place.

Once clip 60 is in place, the relative articulation between clamp extenders 18 and clamping elements 20 may be obtained by simply rotating clamp elements 20 about joints 4 until the desired position is obtained. Then, as shown in FIG. 4, the lower cuff portion 30 may be rotated to a desired rotative displacement relative to handles 14 and 15 and their associated upper cuff portion 31. Once the desired rotative displacement is obtained, handle elements 14 and 15 are urged towards their opposing members such that cuff member 31 is urged downwardly along sleeve 33 and frictionally engages cuff member 30. This engagement between the cuff members limits their relative rotative displacement. Simultaneously with the engagement between cuff members 31 and 30, spindle 12 is forced upwardly by the action of fixed collar 34. This upward movement of spindle 12 acts to slide collar 32 upwardly along clamp extenders 18 so as to move them towards each other. In this manner, clamp elements 20 are also moved together to clamp against clip 60. The engagement between the semi-spherical protrusions on the inner surface of the jaw elements 80 of clamping element 20 and the circular openings on the sides of the surgical clip 60 provides an attachment between the clamping device and the surgical clip 60 which is secure while at the same time fully articulable in terms of pivoting capability, particularly due to the very limited extent to which the protrusions engage in the circular openings of the clip 60.

FIG. 6 is an enlarged side view of the jaw elements 80 of clamping elements 20 engaged with placeable surgical clip 60.

The engaging means of the clamping element 20 of the clamping device is shown with the surgical clip 60 in place, the engaging means comprised of two semi-spherical protrusions 100 extending inward toward each other from the inner surface of the jaw elements 80. Each protrusion 100 has a much larger diameter than the diameter of the circular openings in the sides of the surgical clip 60, so that only a very small, slightly convex segment of each of the semi-spherical protrusions 100 are inserted into the circular openings, allowing a secure attachment while at the same time allowing maximum ease of engagement, manipulation and release of the clamping device 20 from the surgical clip 60. In particular, this method of attachment allows easy pivoting of the clamping device 20 while it is engaged with the surgical clip 60 permitting greater facility in positioning the clamp 20 for use.

What is claimed is:

1. A clamping device comprising:

clamping means including opposed members mounted for movement generally toward and away from each other between a clamping position and a released position;

a support means and means mounting said clamping means on said support means for rotation with respect to said support means, said support means including actuating means movable with respect to said clamping means between a first position wherein said opposed members are moved to said clamping position and a second position wherein said opposed members are moved to said released position said opposed members comprising a pair of longitudinal elements, each element having a jaw end and a connecting end, said longitudinal elements being connected to each other along points thereof by a scissors joint, said connecting ends articulatedly being connected to said mounting means;

said actuating means comprising a pair of articulated handle elements having first and second ends, said second ends being hingedly connected to said support means;

said support means comprising a spindle element having first and second ends connected at said second end to a sliding collar, said sliding collar slidingly engaging said longitudinal elements and moving said elements between said clamping position and said released position;

said mounting means comprising first and second rotation collars, said first and second rotation collars being mounted along said spindle for independent rotational movement thereabout, said first collar hingedly connected to said second ends of said handle elements, said second collar being hingedly connected to said connecting ends;

said engaging means comprising two appendages with semi-spherical ends extending towards each other from the inside of the two said jaw ends of said clamping means;

said engaging means providing an articulating means which, in use, engages a surgical clip in two circular apertures on opposite sides of said surgical clip;

said semi-spherical ends having a greater diameter than the diameter of said circular apertures, limiting the extent to which said appendages are insertable into said circular apertures.

2. A clamping device as in claim 1, wherein
each of said jaw ends has an engaging means including smoothly curved protrusions for cooperation with circular openings provided in a manipulating end of a clipping device.

* * * * *